(12) United States Patent
Hillebrand

(10) Patent No.: US 8,735,068 B2
(45) Date of Patent: May 27, 2014

(54) METHOD AND TEST KIT COMPRISING CITRIC ACID SALT AND ALCOHOL IN A BINDING BUFFER FOR THE SEPARATION, PURIFICATION AND RECYCLING OF LONG- AND SHORT-CHAIN NUCLEIC ACIDS

(75) Inventor: Timo Hillebrand, Hoenow (DE)

(73) Assignee: AJ Innuscreen GmbH, Berlin (DE)

( * ) Notice: Subject to any disclaimer, the term of this patent is extended or adjusted under 35 U.S.C. 154(b) by 0 days.

(21) Appl. No.: 12/774,921

(22) Filed: May 6, 2010

(65) Prior Publication Data

US 2010/0222562 A1  Sep. 2, 2010

Related U.S. Application Data

(63) Continuation of application No. 12/135,465, filed on Jun. 9, 2008, now abandoned, which is a continuation of application No. PCT/EP2006/069451, filed on Dec. 7, 2006.

(30) Foreign Application Priority Data

Dec. 7, 2005 (DE) .................. 10 2005 059 217

(51) Int. Cl.
  *C12Q 1/68* (2006.01)
  *C12P 19/34* (2006.01)
  *C07H 21/04* (2006.01)

(52) U.S. Cl.
  USPC .................. 435/6.12; 435/91.2; 536/23.1

(58) Field of Classification Search
  None
  See application file for complete search history.

(56) References Cited

U.S. PATENT DOCUMENTS

| | | | | |
|---|---|---|---|---|
| 6,586,006 | B2 * | 7/2003 | Roser et al. | 424/484 |
| 7,115,719 | B2 * | 10/2006 | Paulsen | 530/427 |
| 7,803,529 | B1 * | 9/2010 | Cantor et al. | 435/6.12 |
| 2001/0041332 | A1 * | 11/2001 | Hillebrand et al. | 435/6 |
| 2005/0171333 | A1 * | 8/2005 | Paulsen | 530/300 |
| 2006/0160085 | A1 * | 7/2006 | Hillebrand et al. | 435/6 |
| 2006/0166223 | A1 * | 7/2006 | Reed et al. | 435/6 |

FOREIGN PATENT DOCUMENTS

| | | | |
|---|---|---|---|
| WO | WO 89/08257 | 9/1989 | |
| WO | WO 99/54340 | 10/1999 | |
| WO | WO 00/34463 | 6/2000 | |
| WO | WO 02/04620 | 1/2002 | |
| WO | WO 2004/042058 | 5/2004 | |
| WO | WO 2004/042058 A2 * | 5/2004 | ............ C12N 15/10 |
| WO | WO 2004/055207 | 7/2004 | |

OTHER PUBLICATIONS

Sarracino et al., Quantitative MALDI-TOF MS of Oligonucleotides and a Nuclease Assay, Bioorganic & Medicinal Chemisty Letters, vol. 6, No. 21, pp. 2543-2548, 1996.*
S. Lakshmi, et al., "Studies on the Chaotropically Solubilized Arylsulfatase C and Estrone Sulfatase of Sheep Brain", Biochimica et Biophysics Acia, 567 (1979) 184-195.
Samuel R. Farrah, "Chemical Factors Influencing Adsorption of Bacteriophage MS2 to Membrane Filters", Applied and Environmental Microbiology, Mar. 1982, pp. 659-663.
Alex Eon-Duval, et al., "Precipitation of RNA Impurities With High Salt in a Plasmid DNA Purification Process: Use of Experimental Design to Determine Reaction Conditions", Biotechnology and Bioengineering, Bd. 83, Nr. 5, Sep. 5, 2003.
Alex Eon-Duval et al., "Precipitation of RNA Impurities With High Salt in a Plasmid DNA Purification Process: Use of Experimental Design to Determine Reaction Conditions", Wiley Periodicals, Inc. (2003) pp. 1-10.
S. Lakshmi et al., "Studies On The Chaotropically Solubilized Arylsulfatase C and Estrone Sulfatase Of Sheep Brain", Biochimica et Biophysica Acta, 567 (1979) pp. 184-195.

* cited by examiner

*Primary Examiner* — Prabha Chunduru
(74) *Attorney, Agent, or Firm* — Oblon, Spivak, McClelland, Maier & Neustadt, L.L.P.

(57) ABSTRACT

Long- and/or short-chain nucleic acids are separated, purified and recovered by binding the nucleic acid to a solid phase using a binding buffer, to obtain a bonded nucleic acid, and eluting of the bonded nucleic acid from the solid phase, wherein the binding buffer comprises at least one citric acid salt and at least one alcohol.

21 Claims, No Drawings

METHOD AND TEST KIT COMPRISING CITRIC ACID SALT AND ALCOHOL IN A BINDING BUFFER FOR THE SEPARATION, PURIFICATION AND RECYCLING OF LONG- AND SHORT-CHAIN NUCLEIC ACIDS

BACKGROUND OF THE INVENTION

1. Field of the Invention

The invention relates to a novel buffer formulation for fast separation, purification and highly efficient recovery of long- and/or short-chain nucleic acids.

2. Discussion of the Background

A multiplicity of commercially-available kits exist today for the purification and recovery of specific DNA fragments.

All of these methods are based on a method for the preparative and analytical purification of DNA fragments from agarose gels developed and described for the first time by Vogelstein and Gillespie (Proc. Natl. Acad. Sci. USA, 1979, 76, 615-619). The method combines the break-up (in a saturated solution of a chaotropic salt (NaI)) of the agarose containing the bands of the DNA to be isolated with binding of the DNA to glass particles. The DNA fixed to the glass particles is then washed with a wash solution (20 mM Tris HCl [pH 7.2]; 200 mM NaCl; 2 mM EDTA; 50% v/v ethanol) and finally separated from the support particles.

The physico-chemical principle of the systems for isolating nucleic acids on the basis of the binding of nucleic acids to the surfaces of mineral supports, adopted and commercially available today according to the background art, should thereby consist in the disruption of superordinate structures of the aqueous medium, through which the nucleic acids on the surface of mineral materials, in particular of glass or silica particles, adsorb. The disruption of the superordinate structures of the aqueous medium is thereby always carried out in the presence of chaotropic ions and is almost quantitative at high concentrations of these. On this physico-chemical basis described, all commercially available systems for the isolation of nucleic acids contain buffer compositions with higher ion strengths of chaotropic salts, for the binding of nucleic acids to a nucleic acid-binding solid phase.

All the methods described for the isolation of nucleic acids by the binding of nucleic acids to mineral solid phases by the use of chaotropic salt solutions have in common the fact that for the binding of the nucleic acids to the support materials used, high concentrations must be adopted. At the same time, chaotropic salts (e.g. guanidine thiocyanate, guanidine hydrochloride, sodium perchlorate or sodium iodide) are highly toxic potent substances. The buffer systems with very high ion strengths being used often effect a diversion of salt contaminations, which can prove problematic for a string of downstream applications. What is more, in association with chaotropic buffers there exists a considerable health risk (in particular in long-term use) as well as a considerable environmental effect through quantities of toxic substances dumped into effluent water.

Interestingly, it turns out that all systems which are commercially available worldwide for isolating nucleic acids on the basis of binding of nucleic acids to mineral support materials (magnetic particles, membranes, carrier suspensions et al.) work, in principle, according to the method described. Since the first description by Vogelstein and Gillespie, the bound nucleic acids have always been washed with alcohol or salt solutions containing acetone. The wash steps are essential components of the extraction protocols and, alongside the removal of bound, undesired, inhibiting substances, always also serve in the necessary removal of the salts necessary for the binding of the nucleic acids.

In WO 01/62976 A1, a description is disclosed which comprises the purification of nucleic acids from various reaction assays upon addition of different alcohols, their subsequent precipitation on special solid phases (membranes with specific physical characteristics), wash steps with alcoholic buffers and the final elution of the nucleic acids by means of water.

U.S. Pat. No. 5,405,951 A and EP 0512767 A1 likewise describe the isolation of nucleic acids by incubation of the sample containing nucleic acids with an alcohol, and the subsequent incubation of the sample with a mineral material. The elution of the nucleic acids is carried out upon the addition of water heated to 60° C.

In DE 10253351 A1, it is disclosed that the purification and recovery of nucleic acids is carried out by adjusting the solution containing nucleic acid with additives in such a way that it contains monovalent and multivalent cations as well as an alcohol, brings them afterwards into contact with the solid phase, subsequently washes the support and releases the nucleic acid from the solid phase. Ammonium chloride, sodium chloride and/or calcium chloride are used as monovalent salt components, and magnesium chloride, calcium chloride, zinc chloride and/or manganese chloride are used as multivalent salt components.

It is disclosed that precisely the combination of a monovalent and of a multivalent salt leads to nucleic acids adsorbing on solid phases, wherein the ion strengths necessary for this must only be very small. This has the advantage, if applicable, that wash steps which were always necessary until now are no longer required, and so the methods for isolating nucleic acids can be clearly shortened and simplified.

At the same time, it emerges that on use of buffer combinations given in DE 10253351 A1 (e.g. magnesium chloride/calcium chloride), the purification and recovery of DNA fragments from PCR reaction mixtures certainly takes place at a high recovery rate, but unfortunately no selective removal of undesired PCT by-products (e.g. primer-dimers) is possible.

For this reason, only the general possibility of the recovery of DNA fragments can be demonstrated, but not their efficient purification. The cause of this observation thereby seems to possibly be the multivalent cation used. If, however, the multivalent cation is removed from the buffer mixture, then the recovery of nucleic acids with the buffers described is no longer possible on the basis of the very small ion strengths. However, the use of buffers with only very small ion strengths was precisely the inventive purpose of the patent specification.

WO/34463 A1 describes a method for isolating nucleic acids, in which the nucleic acids are bound to a solid phase, wherein the conveyance of the binding is carried out by binding buffers on the basis of so-called antichaotropic salts and an alcoholic component. The bound nucleic acids are washed with wash buffers known in themselves and finally eluted by the addition of a low-salt buffer. The ion strengths of the so-called antichaotropic salts come to at least 0.1M-10M. The so-called antichaotropic salts for the binding of nucleic acids to a solid phase are, without exception, chlorides.

WO 89/08257 A1 indicates that citrates belong to the group of antichaotropic salts. The property characterized in WO 89/08257 A1 is to be understood in the context of the immobilization of proteins and has no relationship at all to nucleic acids or methods for the isolation and purification of nucleic acids.

DETAILED DESCRIPTION OF THE INVENTION

It is an object of the present invention to eliminate the aforementioned disadvantages of the background art.

This and other objects have been achieved by the present invention as set forth in the claims and specification.

According to the invention, a method and a test kit were produced which allow a highly efficient recovery of both long- and short-chain nucleic acids, and removing of undesired nucleic acids. The method is simple and fast to carry out.

The invention aims particularly at such uses in which specific nucleic acid fragments from complex reaction assays (PCR, restriction assays, sequencing assays, marking assays) are purified and recovered highly efficiently and quickly, in order to convey them to a subsequent reaction.

In the context of the present invention, chaotropic salts are salts that destroy regular structures of liquid water based on the formation of hydrogen bonds, in that they inhibit the formation of $H_2O$ cage structures necessary for solvation. Examples of chaotropic salts are thiocyanates, iodides or perchlorates. They bring about denaturation of proteins, the increase in the solubility of nonpolar substances in water as well as the destruction of the hydrophobic interaction.

In the context of the present invention, antichaotropic components are defined as substances that enhance regular structures of liquid water based on the formation of hydrogen bonds. Examples of antichaotropic components are ammonium, sodium or potassium salts. They do not bring about denaturation, but enhance hydrophobic forces and the increase in hydrophobic interactions.

In the context of the present invention, non-chaotropic components are, for example salts, that are between chaotropic and anti-chaotropic salts, and include for example, magnesium chloride or aluminum chloride. Non-chaotropic compounds do not enhance or destroy regular structures of liquid water based on the formation of hydrogen bonds. Non-chaotropic substances are, for example, those in the middle of the Hofmeister series of salts.

In the context of the present invention, alcoholic components are all water-soluble alcohols such as methanol, ethanol, propanol, isopropanol, ethylene glycol, polyethylene glycol or glycerine. They can be used alone or in combination.

The method according to the invention for the separation, purification and recovery of long- and/or short-chain nucleic acids comprises:
(1) binding the nucleic acids to a solid phase by using a binding buffer, to obtain bonded nucleic acids,
(2) elution of the bonded nucleic acids from the solid phase, wherein the binding buffer comprises a composition of at least one citric acid salt and at least one alcohol as effective components. The binding buffer contains neither chaotropic salts nor a combination of salts with monovalent and multivalent cations. Salts with simply positively-charged cations are preferably introduced as citric acid salts, e.g. corresponding hydrogen citrates or dihydrogen citrates.

According to the invention, the following salts can be introduced alone or in combination of at least two salts:
 a) Di-ammonium hydrogen citrate,
 b) Ammonium dihydrogen citrate,
 c) Tri-sodium citrate,
 d) Di-sodium hydrogen citrate,
 e) Sodium hydrogen citrate,
 f) Tri-potassium citrate,
 g) Di-potassium hydrogen citrate,
 h) Potassium hydrogen citrate.

The alcohol concentrations of the binding buffer are between 20% - 90wt.%, preferably between 40% - 70 wt.%. The alcohol concentration includes all values and subvalues therebetween, especially including 25, 30, 35, 40, 45, 50, 55, 60, 65, 70, 75, 80 and 85 wt.%. Methanol, ethanol, propanol, isopropanol, ethylene glycol, polyethylene glycol or glycerin can be used as alcohols, alone or in combination.

According to the invention, the ion strengths for binding to the solid phase in combination with an alcohol are less than 100 mM, preferably less than 50 mM. The ion strength includes all values and subvalues therebetween, especially including 5, 10, 15, 20, 25, 30, 35, 40, 45, 50, 55, 60, 65, 70, 75, 80, 85, 90 and 95 mM.

The solid phase can comprise glass fibre materials, silica gels, suspensions of mineral supports, functionalised magnetic particles; preferably glass fibre materials having a length of from 0.7 μm to 2 μm.

The method according to the invention for the separation, purification and recovery of long- and/or short-chain nucleic acids includes the following steps:
 addition of a binding buffer to a reaction assay containing at least one nucleic acid, to obtain a mixture,
 transfer of the mixture from the reaction assay and the binding buffer to a solid phase, and
 elution of the nucleic acid bound to the solid phase, and washing of the nucleic acids bound to the solid phase.

In one embodiment, the binding buffer comprises at least one citric acid salt and at least one alcohol.

In one embodiment, the nucleic acids bound to the solid phase are not washed. Even more preferred is a method where no washing is performed at any stage.

Subject of the invention is also a test kit comprising at least one alcohol, at least one citric acid salt, a solid phase and an elution buffer.

The use of citric acid salts in combination with at least one alcohol is the separation, purification and recovery of long- and/or short-chain nucleic acids, in particular of PCR products, restriction assays or sequencing assays.

Surprisingly, the inventor of the present invention has found that various citric acid salts in combination with an alcohol can bind long- and short-chain nucleic acids to support materials, in particular glass fiber materials, and to remove them again.

Surprisingly, the inventor of the present invention has also found that the ion strengths necessary for the binding of the nucleic acids must also only be present in millimolar concentrations. The use of buffer solutions on the basis of an alcohol and of a citric acid salt allows a highly efficient recovery of nucleic acids from reaction assays with simultaneous separation of undesired by-products. This is particularly the case in the purification of PCR products from PCR reaction mixtures, where primers or primer-dimers in particular have to be separated from the specific amplification products.

For example, di-ammonium hydrogen citrate, tri-potassium citrate-monohydrate or tri-sodium citrate-dihydrate are introduced as preferred citric acid salts. Ammonium dihydrogen citrate, di-sodium hydrogen citrate, sodium dihydrogen citrate, di-potassium hydrogen citrate, potassium dihydrogen citrate can also be introduced. The citrates can be used alone or in combination. The ion strengths necessary for the binding are smaller than 100 mM, preferably smaller than 50 mM. The required alcohol concentrations of the binding buffer are between 20%-90 wt. %, preferably between 40%-70 wt. %. Different alcohols can be introduced; preferably isopropanol is used.

In one embodiment, the method according to the invention for the purification and recovery of DNA fragments from reaction assays is extremely fast and simple to carry out. The reaction assays from which the nucleic acid(s) have to be purified, are mixed with the binding buffer according to the invention and subsequently conveyed to a centrifuge column (e.g. with a glass fibre material) and centrifuged. Afterwards, the centrifuge column is brought into a new collecting vessel and the DNA fragments eluted by the column surface after addition of water or a low salt buffer (10 mM Tris HCL).

In contrast to the method (kits) finding commercial use, no wash steps are necessary. Moreover, the method does entirely without chaotropic salts which are hazardous to health or the environment, as have been adopted until now in commercially-available methods.

What is more, the amount of time spent on a purification reaction can be drastically reduced. A purification can be completed in approx. 3 min, as a rule.

The method makes possible the purification and recovery of a broad spectrum of sizes of DNA fragments with a very high recovery rate.

Surprisingly, the inventor of the present invention has found that the combination according to the invention of the citric acid salts influences, in terms of ion strength, both the efficiency of the recovery as well as the selectivity regarding the DNA fragments to be purified regarding their fragment length. This observation can be excellently used to develop new areas of application. So the method according to the invention also makes possible an efficient purification of PCR products, restriction assays or sequencing assays. In the case of sequencing assays, the task is to efficiently separate dye-terminators, with simultaneous efficient recovery of the nucleic acid fragments of a wide molecular weight spectrum, in particular also the recovery of very small nucleic acid fragments. The implementation of this task-setting likewise requires only 3 min and is therefore very clearly simpler and faster than all other methods being used until now.

The difference between the present invention and the solution suggested in WO/34463 consists in the fact, among others, that in the present invention, the ion strengths are smaller than 0.1 M, preferably smaller than 0.05 M. The use of citric acid salts is not disclosed in WO/34463. This is also explicable as the uses mentioned in WO/34463 cannot at all be carried out with citric acid salts. The present invention however refers to citric acid salts. WO/34463 describes, without exception, methods for the isolation and purification of genomic nucleic acids which are isolated from complex biological samples. But it does not describe a method which makes possible the purification and recovery of a nucleic acid already present. For this reason, the isolation of the nucleic acids is also always carried out with buffers which, alongside a salt component, also contain detergents, proteolytic enzymes as well as further additives, the function of which consists in the digestion (lysis) of the biological sample.

The present invention does not refer to the isolation of genomic nucleic acids from complex biological samples. The subject of the present invention is the purification of reaction assays, e.g. PCR reaction assays, wherein subsequently e.g. an amplified DNA fragment with a high recovery rate has to be recovered. No lysis of a biological sample takes place, in the sense in which this is implemented with the buffers of WO/34463. WO/34463 describes, without exception, a method for the isolation and purification of genomic nucleic acids, which contains as an obligatory step the washing (several times) of the nucleic acids bound to the solid phase. Washing is not only necessary in WO/34463 in order to remove inhibiting substances from the biological samples, it is also necessary in order to wash out the high salt concentrations of the binding buffer used. The analysis of the exemplary embodiments shows that the lysis/binding buffers have ion strengths of >1.5 M, as a rule. The present invention uses clearly smaller salt concentrations (less than 0.1 M). For these reasons, the advantage according to the invention also consists in getting by without wash steps which have been necessary until now, and thereby clearly simplifying and shortening the operation.

What is more, in the background art there is generally no indication that citric acid salts are adopted for binding nucleic acids to mineral solid phases. The invention is, however, based on precisely this observation, all the more so that precisely these salts make it possible to implement a binding of nucleic acids even in the presence of ion strengths of less than 100 mM, in particular less than 50 mM. The salts WO/34463 described do not allow for any binding of nucleic acids and their quantitative recovery if they were to be introduced in these low ion strengths.

WO 89/08257 A1 indicates that citrates belong to the group of antichaotropic salts. The property characterized in this application is to be understood in the context of the immobilization of proteins and has no relationship at all to nucleic acids or methods for the isolation and purification of nucleic acids.

Other documents alongside the one already described in detail (WO/34463 A1) also describe the use of so-called antichaotropic as well as chaotropic salts for the isolation and purification of nucleic acids. To this extent it is also not the goal of the present invention to use antichaotropic salts and their application in nucleic acid isolation, but rather much more to create the possibility of using firstly the combination of citric acid salts and an alcohol in extremely small ion strengths for an efficient purification and subsequent quantitative recovery of nucleic acids, and thereby of nucleic acid fragments. And this was not known until now.

Having generally described this invention, a further understanding can be obtained by reference to certain specific examples which are provided herein for purposes of illustration only, and are not intended to be limiting unless otherwise specified.

EXAMPLES

Purification and recovery of a PCR product of 98 by from a PCR reaction mixture. Use of different binding buffers.

Buffer 1: 50 mM di-ammonium hydrogen citrate/62% isopropanol.
Buffer 2: 50 mM tri-sodium citrate-dihydrate/62% isopropanol.
Buffer 3: 50 mM tri-calcium citrate-monohydrate/62% isopropanol.
Buffer 4: 25 mM di-ammonium hydrogen citrate/62% isopropanol.
Buffer 5: 25 mM tri-sodium citrate-dihydrate/62% isopropanol.
Buffer 6: 25 mM tri-calcium citrate-monohydrate/62% isopropanol.

In each case, 500 µl of the binding buffer were mixed with 50 µl of a PCR assay with an amplified fragment of 98 bp.

The mixture was subsequently conveyed to a centrifugation column with a glass fibre filter (AF; Fa. Pall), in order to connect the desired nucleic acid fragment, and centrifuged at 10 000×g for 1 min. The centrifugation column was then inserted into a new 1.5 ml reaction vessel and centrifuged again for 1 min at 8000×g after addition of an elution agent (10 mM Tris-HCL).

The eluted PCR fragments were subsequently analysed on an Agilent Bioanalyzer, and the purity as well as the recovery rates were determined in relation to the non-purified PCR assays.

No more unspecific primers and primer-dimers could be detected.

The following table contains the recovery rates for each of the different binding buffers P1-P6.

| Output fragment; not purified | Binding buffer P1 | Binding buffer P2 | Binding buffer P3 | Binding buffer P4 | Binding buffer P5 | Binding buffer P6 |
| --- | --- | --- | --- | --- | --- | --- |
| 100% | 83.5% | 78.5% | 76.9% | 87.8% | 74.4% | 82.6% |

The example clearly illustrates that very high recovery rates can be achieved with the binding buffers according to the invention.

German patent application DE 10 2005 059 217.1 filed Dec. 7, 2005, and international patent application PCT/EP2006/069451, filed Dec. 7, 2006, are incorporated herein by reference.

Numerous modifications and variations on the present invention are possible in light of the above teachings. It is therefore to be understood that within the scope of the appended claims, the invention may be practiced otherwise than as specifically described herein.

The invention claimed is:

1. A method for separating, purifying or recovering a long- and/or short-chain nucleic acid, comprising:
    binding the nucleic acid to a solid phase by using a binding buffer to obtain a bonded nucleic acid; and
    eluting the bonded nucleic acid from the solid phase thereby separating, purifying or recovering the long- and/or short-chain nucleic acid;
    wherein the binding buffer has a salt concentration of less than 100 mM and comprises
        at least one non-chaotropic citric acid salt and
        at least one alcohol in an amount ranging from 20 wt. %-90 wt. %; and
        wherein the binding buffer comprises neither (i) a chaotropic salt, nor (ii) a combination of a salt with a monovalent cation and a salt with a multivalent cation.

2. The method according to claim 1, wherein the non-chaotropic citric acid salt represents a salt with a singly positively charged cation.

3. The method according to claim 1, wherein a hydrogen citrate or a dihydrogen citrate or a mixture thereof is introduced as the non-chaotropic citric acid salt.

4. The method according to claim 1, wherein the non-chaotropic citric acid salt is selected from the group consisting of di-ammonium hydrogen citrate, ammonium dihydrogen citrate, tri-sodium citrate, di-sodium hydrogen citrate, sodium hydrogen citrate, tri-potassium citrate, di-potassium hydrogen citrate, potassium hydrogen citrate and mixtures thereof.

5. The method according to claim 1, wherein an alcohol concentration of the binding buffer is between 40 wt. % to 70 wt. %.

6. The method according to claim 1, wherein said alcohol is at least one selected from the group consisting of methanol, ethanol, propanol, isopropanol and mixtures thereof.

7. The method according to claim 1, wherein said alcohol is at least one selected from the group consisting of ethylene glycol, polyethylene glycol, glycerin and mixtures thereof.

8. The method according to claim 1, wherein the binding buffer consists essentially of a citric acid salt buffer that has a citric acid salt concentration of 50 mM to less than 100 mM.

9. The method according to claim 1, wherein the binding buffer consists essentially of a citric acid salt buffer that has a citric acid salt concentration of 25-50 mM.

10. The method according to claim 1, wherein said solid phase is selected from the group consisting of a glass fibre material, a silica gel, a suspension of a mineral support, a functionalized magnetic particle and combinations thereof.

11. The method according to claim 1, wherein said solid phase is a glass fibre material having a length of 0.7 μm to 2 μm.

12. A method for separating, purifying or recovering a long- and/or short-chain nucleic acid, comprising:
    contacting a mixture containing a nucleic acid sample and a binding buffer which has a salt concentration of less than 100 mM with a solid phase under conditions suitable for binding of the nucleic acid to the solid phase; and
    eluting said nucleic acid from said solid phase thereby separating, purifying or recovering the long- and/or short-chain nucleic acid;
    wherein the binding buffer comprises at least one non-chaotropic citric acid salt and at least one alcohol in an amount ranging from 20 wt. % to 70 wt. %; and
    wherein the binding buffer comprises neither (i) a chaotropic salt, nor (ii) a combination of a salt with a monovalent cation and a salt with a multivalent cation.

13. The method according to claim 12, which does not comprise washing of the nucleic acids bound to the solid phase.

14. The method according to claim 12, wherein the citric acid salt represents a salt with a singly positively charged cation.

15. The method according to claim 12, wherein a hydrogen citrate or a dihydrogen citrate or a mixture thereof is introduced as citric acid salt.

16. The method according to claim 12, wherein the citric acid salt is selected from the group consisting of di-ammonium hydrogen citrate, ammonium dihydrogen citrate, tri-sodium citrate, di-sodium hydrogen citrate, sodium hydrogen citrate, tri-potassium citrate, di-potassium hydrogen citrate, potassium hydrogen citrate and mixtures thereof.

17. The method according to claim 12, wherein the alcohol concentration of the binding buffer is between 40 wt. %-70 wt. %.

18. The method according to claim 12, wherein said alcohol is methanol, ethanol, propanol, isopropanol, ethylene glycol, polyethylene glycol, glycerin or mixtures thereof.

19. The method according to claim 12, wherein said solid phase is selected from the group consisting of a glass fibre material, a silica gel, a suspension of a mineral support, a functionalized magnetic particle and combinations thereof.

20. The method according to claim 12, wherein said solid phase is a glass fibre material having a length of 0.7 μm to 2 μm.

21. A method for the purification of a nucleic acid obtained from PCR, a restriction assay, or a sequencing assay, comprising:
    contacting said nucleic acid with the components of a test kit, and recovering a purified nucleic acid;
    wherein the test kit comprises
    a binding buffer that has salt concentration of less than 100 mM and that comprises at least one non-chaotropic citric acid salt and at least one alcohol in an amount ranging from 20 wt. %-90 wt. %; wherein the binding buffer comprises neither (i) a chaotropic salt, nor (ii) a combination of a salt with a monovalent cation and a salt with a multivalent cation;

a solid phase; and an elution buffer.

\* \* \* \* \*